(12) United States Patent
Wright (10) Patent No.: US 11,752,199 B1
(45) Date of Patent: Sep. 12, 2023

(54) METHODS OF MODULATING PERICYTES (71) Applicant: MALLINCKRODT ARD IP UNLIMITED COMPANY, Dublin (IE)

(72) Inventor: Dale Wright, Hazelwood, MO (US)

(73) Assignee: MALLINCKRODT ARD IP UNLIMITED COMPANY, Dublin (IE)

( * ) Notice: Subject to any disclaimer, the term of this patent is extended or adjusted under 35 U.S.C. 154(b) by 143 days.

(21) Appl. No.: 17/185,586

(22) Filed: Feb. 25, 2021

Related U.S. Application Data (60) Provisional application No. 62/981,283, filed on Feb. 25, 2020.

(51) Int. Cl.
*A61K 38/00* (2006.01)
*A61K 38/35* (2006.01)
*A61K 9/00* (2006.01)

(52) U.S. Cl.
CPC ............ *A61K 38/35* (2013.01); *A61K 9/0019* (2013.01)

(58) Field of Classification Search
CPC .............................. A61K 38/35; A61K 9/0019
See application file for complete search history.

(56) References Cited

U.S. PATENT DOCUMENTS

| | | | |
|---|---|---|---|
| 4,241,046 A | 12/1980 | Papahadjopoulos et al. | |
| 4,394,448 A | 7/1983 | Szoka, Jr. et al. | |
| 4,529,561 A | 7/1985 | Hunt et al. | |
| 4,554,101 A | 11/1985 | Hopp | |
| 4,755,388 A | 7/1988 | Heath et al. | |
| 4,828,837 A | 5/1989 | Uster et al. | |
| 4,925,661 A | 5/1990 | Juang | |
| 4,954,345 A | 9/1990 | Muller | |
| 4,957,735 A | 9/1990 | Huang | |
| 5,043,164 A | 8/1991 | Huang et al. | |
| 5,064,655 A | 11/1991 | Uster et al. | |
| 5,077,211 A | 12/1991 | Yarosh | |
| 5,264,618 A | 11/1993 | Felgner et al. | |
| 2014/0322226 A1* | 10/2014 | Knight | A61K 9/0043 514/1.5 |

OTHER PUBLICATIONS

Thomas et al. Microscopy Research and Technique 61:247-251 (2003).*
Jack Kyte and Russell F. Doolittle; "A Simple Method for Displaying the Hydropathic Character of a Protein", J. Mol. Biol., 1982, 157, pp. 105-132.
Martin A. Schwartz, Dietmar Vestweber, and Michael Simons; "Blood Vessel Stability vs. Instability: a Unifying Concept in Vascular Health and Disease", HHS Public Access; Author manuscript; Science; available in PCM Dec. 16, 2018; 5 pages.
Acthar Gel Product Information Sheet; Mar. 2019; 4 pages.

* cited by examiner

*Primary Examiner* — Jeanette M Lieb (57) ABSTRACT

The present disclosure is directed to methods of modulating pericytes in subjects in need thereof.

12 Claims, 2 Drawing Sheets
(1 of 2 Drawing Sheet(s) Filed in Color)
Specification includes a Sequence Listing.

SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: SYNTHESIZED

<400> SEQUENCE: 1

```
Ser Tyr Ser Met Glu His Phe Arg Trp Gly Lys Pro Val Gly Lys Lys
1               5                   10                  15

Arg Arg Pro Val Lys Val Tyr Pro Asp Gly Ala Glu Asp Gln Leu Ala
            20                  25                  30

Glu Ala Phe Pro Leu Glu Phe
        35
```

METHODS OF MODULATING PERICYTES

CROSS REFERENCE TO RELATED APPLICATIONS

This application claims the priority of U.S. provisional application No. 62/981,283, filed Feb. 25, 2020, which is hereby incorporated by reference in its entirety.

FIELD OF THE DISCLOSURE

The present disclosure is directed to methods of modulating pericytes in subjects in need thereof.

REFERENCE TO SEQUENCE LISTING

This application contains a Sequence Listing that has been submitted in ASCII format via EFS-Web and is hereby incorporated by reference in its entirety. The ASCII copy, created on Feb. 25, 2021, is named 682036_SequenceListing_ST25, and is 1000 bytes in size.

BACKGROUND

Pericytes are cells that wrap around endothelial cells throughout the body. They are regulatory cells that maintain vascular stability, tissue homeostasis, and hemostasis during both development and adulthood. They aid in the regulation of blood flow and maintenance of homeostasis within the body. They are essential for the regulation of the vascular system and serve as vital integrators, coordinators and effectors of many vascular functions, including angiogenesis, blood-brain barrier (BBB) formation and maintenance, and vascular stability. In the brain, vascular homeostasis is critical for survival and is maintained through a complex series of cross talk mechanisms that involve the cells of the neurovascular unit. Perturbation of these cross-talk mechanisms leads to loss of blood brain barrier (BBB) integrity and can lead to neuronal hyperactivity. Vascular dysfunction may also cause CNS disease and may have a role in development of seizure disorders as well as other classic neurodegenerative diseases. Studies have suggested that a pericyte deficiency in the CNS leads to BBB breakdown and brain hypoperfusion resulting in secondary neurodegenerative changes. Pericytes also are very important during tissue development, tissue regeneration and contribute to the healing processes (Int J Cardiol. 2015;190: 75-89)

SUMMARY

Among the various aspects of the present disclosure are provided methods of modulating pericytes in subjects in need thereof.

One aspect provides methods of promoting new vessel formation in a subject in need thereof, the method comprising administering an adrenal corticotropin treatment. In some embodiments, the adrenal corticotropin treatment comprises a repository corticotropin injection (RCI). In some embodiments, the repository corticotropin injection is a naturally sourced complex mixture of adrenocorticotropic hormone analogs and other pituitary peptides. In particular embodiments, the respository corticotropin injection comprises N-25 deamidated porcine ACTH (1-39).

One aspect provides methods of increasing angiopoietin-2 expression in pericytes, the method comprising contacting pericytes with an adrenal corticotropin treatment. In some embodiments, the adrenal corticotropin treatment comprises a repository corticotropin injection (RCI). In some embodiments, the repository corticotropin injection is a naturally sourced complex mixture of adrenocorticotropic hormone analogs and other pituitary peptides. In particular embodiments, the respository corticotropin injection comprises N-25 deamidated porcine ACTH (1-39).

One aspect provides methods of increasing VCAM-1 expression in pericytes, the method comprising contacting pericytes with an adrenal corticotropin treatment. In some embodiments, the adrenal corticotropin treatment comprises a repository corticotropin injection (RCI). In some embodiments, the repository corticotropin injection is a naturally sourced complex mixture of adrenocorticotropic hormone analogs and other pituitary peptides. In particular embodiments, the respository corticotropin injection comprises N-25 deamidated porcine ACTH (1-39).

One aspect provides methods of slowing vessel degradation in a subject in need thereof, the method comprising administering an adrenal corticotropin treatment to the subject. In some embodiments, the adrenal corticotropin treatment comprises a repository corticotropin injection (RCI). In some embodiments, the repository corticotropin injection is a naturally sourced complex mixture of adrenocorticotropic hormone analogs and other pituitary peptides. In particular embodiments, the respository corticotropin injection comprises N-25 deamidated porcine ACTH (1-39).

One aspect provides methods of increasing vascular stability in a subject in need thereof, the method comprising administering an adrenal corticotropin treatment to the subject. In some embodiments, the adrenal corticotropin treatment comprises a repository corticotropin injection (RCI). In some embodiments, the repository corticotropin injection is a naturally sourced complex mixture of adrenocorticotropic hormone analogs and other pituitary peptides. In particular embodiments, the respository corticotropin injection comprises N-25 deamidated porcine ACTH (1-39).

One aspect provides methods of increasing the number of pericytes, the method comprising contacting a pericyte with an adrenal corticotropin treatment. In certain embodiments, the pericyte number is increased in vivo. In some embodiments, the adrenal corticotropin treatment comprises a repository corticotropin injection (RCI). In some embodiments, the repository corticotropin injection is a naturally sourced complex mixture of adrenocorticotropic hormone analogs and other pituitary peptides. In particular embodiments, the respository corticotropin injection comprises N-25 deamidated porcine ACTH (1-39).

One aspect provides methods of increasing pericyte longevity, the method comprising contacting the pericyte with an adrenal corticotropin treatment. In certain embodiments, the pericyte number is increased in vivo. In some embodiments, the adrenal corticotropin treatment comprises a repository corticotropin injection (RCI). In some embodiments, the repository corticotropin injection is a naturally sourced complex mixture of adrenocorticotropic hormone analogs and other pituitary peptides. In particular embodiments, the respository corticotropin injection comprises N-25 deamidated porcine ACTH (1-39).

One aspect provides methods of stabilizing the blood brain barrier in a subject in need thereof, the method comprising administering an adrenal corticotropin treatment to the subject. In some embodiments, the adrenal corticotropin treatment comprises a repository corticotropin injection (RCI). In some embodiments, the repository corticotropin injection is a naturally sourced complex mixture of adrenocorticotropic hormone analogs and other pituitary peptides.

In particular embodiments, the respository corticotropin injection comprises N-25 deamidated porcine ACTH (1-39).

These and other aspects and iterations of the invention are described more thoroughly below.

DESCRIPTION OF THE FIGURES

The application file contains at least one drawing executed in color. Copies of this patent application publication with color drawing(s) will be provided by the Office upon request and payment of the necessary fee.

DETAILED DESCRIPTION

The present disclosure encompasses methods of treating a subject in need of treatment. Generally speaking, the methods comprise administering an adrenal corticotropin treatment to the subject in need thereof.

I. TREATMENTS

Methods of the present disclosure encompass the use and administration of adrenal corticotropin treatment(s) to a subject. Such treatments are described below.

Generally speaking, an adrenal corticotropin treatment refers to a treatment that mimics the physiological activity of adrenocorticotropic hormone (ACTH). ACTH is a 39 amino acid peptide hormone that is secreted by the pituitary gland and is a part of the hypothalamus-pituitary-adrenal (HPA) axis that maintains the stress response and homeostasis in the body. Physiologically, the principal effects of ACTH are stimulation of the adrenal cortex with subsequent increased production of glucocorticosteroids and/or cortisol from the adrenal cortex. ACTH levels are tightly regulated in the body via a negative feedback loop wherein glucocorticosteroids suppress the release of corticotropin release hormone (CRH) from the pituitary and CRH-mediated release of ACTH. In some instances, cortisol helps restore homeostasis after stress. In some instances, changed patterns of serum cortisol levels are observed in connection with abnormal ACTH levels. In some instances, prolonged ACTH-mediated secretion of abnormal levels of cortisol (e.g., higher or lower levels of cortisol compared to cortisol levels in normal individuals) has detrimental effects. Thus, any perturbation in the levels of ACTH has profound physiological implications.

In vivo, ACTH is synthesized from a precursor polypeptide pre-pro-opiomelanocortin (pre-POMC). The removal of the signal peptide during translation produces a 267 amino acid polypeptide POMC. POMC undergoes a series of post-translational modifications to yield various polypeptide fragments including and not limited to ACTH, β-lipotropin, γ-lipotropin, α, β, γ-Melanocyte Stimulating Hormone (MSH) and β-endorphin. POMC, ACTH and β-lipotropin are also secreted from the pituitary gland in response to the hormone corticotropin-releasing hormone (CRH). The first 13 amino acids of $ACTH_{1-39}$ are cleaved to form α-melanocyte-stimulating hormone (α-MSH).

In some instances, an abnormality in ACTH levels is associated with inflammation (e.g., increased release of pro-inflammatory cytokines). In some instances, an abnormality in ACTH levels is associated with reduced VEGF secretion. In some instances, reduced VEGF secretion is associated with reduced growth of new blood vessels and inadequate oxygen supply to tissues (e.g., neurons and/or muscles).

In some embodiments of the uses or methods described herein, the ACTH peptide is a $ACTH_{1-39}$ peptide having the formula:

or a fragment thereof, a variant thereof or any combination thereof.

In some embodiments, an adrenal corticotropin treatment may comprise a synthetic adrenal corticotropin composition. In other embodiments, an adrenal corticotropin treatment may comprise a non-synthetic adrenal corticotropin composition. Both of these embodiments are described in more detail below.

(a) synthetic adrenal corticotropin composition

As used herein, the phrase "synthetic adrenal corticotropin composition" refers to a composition comprising an ACTH peptide, homolog, variant, aggregate, complex, preparation, or prodrug that has been recombinantly produced or otherwise synthesized. The phrase "synthetic adrenal corticotropin composition" excludes compositions comprising an ACTH peptide, homolog, variant, aggregate, complex, or preparation naturally, endogenously, produced in a cell of an organism.

A synthetic adrenal corticotropin composition may include corticotropin, tetracosactide or the like. In some embodiments, a synthetic adrenal corticotropin composition may include any synthetically produced ACTH peptide, ACTH fragment, or ACTH preparation as described herein.

The term "ACTH peptide" refers to $ACTH_{1-39}$ peptide. The term "ACTH peptide homolog" includes ACTH peptide or peptide fragments or ACTH-like compounds with about 40%, about 45%, about 50%, about 55%, about 60%, about 65%, about 70%, about 75%, about 80%, about 85%, about 90%, or about 95% sequence identity with $ACTH_{1-39}$.

As used herein the term "variant" may mean a peptide or polypeptide that differs in amino acid sequence by the insertion, deletion, or conservative substitution of amino acids, but retains at least one biological activity. A variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

The phrase "ACTH peptide, fragment, variant, or prodrug" also includes, in certain embodiments, pre-POMC, POMC, β-lipotropin, γ-lipotropin, Melanocyte Stimulating Hormone (α-MSH, β-MSH, γ-MSH), β-endorphin, or the like, or any other polypeptide fragment that is a post-translational product of the POMC gene. POMC genes for various species are found in the NCBI GenBank including and not limited to human POMC transcript variant 1, mRNA, (NCBI Accession number NM_001035256), human POMC transcript variant 2, mRNA, (NCBI Accession number NM_000939), swine pro-opiomelanocortin, mRNA (NCI Accession number S73519), swine proopiomelanocortin protein (POMC) gene (NCBI Accession number EU184858), rat proopiomelanocortin (POMC) gene (NCBI Accession number K01877), or the like. Other examples of POMC genes include, for example, catfish POMC gene described in Animal Genetics, 2005, 36, 160-190. Melanocortin peptides, including ACTH and alpha, beta, and gamma MSH, derive from post-translational modification of POMC. A number of melanocortin peptides share an invariant sequence of four amino acids, His-Phe-Arg-Trp, which also correspond to residues 6-9 of ACTH and alpha-MSH. Accordingly, also contemplated within the scope of embodiments presented herein, is the use of amino acid sequences that correspond to alpha MSH, beta MSH or gamma MSH. See Catania et al., Pharmacol. Rev. 2004, 56: 1-29.

The term "ACTH aggregate" refers to a physical grouping of peptides which may comprise ACTH peptide, or fragments, analogs or homologs thereof. Such an aggregate may comprise hydrogen-bonded molecules and/or molecules held by bridging interactions via, for example, a salt bridge, a metal ion, and the like.

The term "ACTH complex" refers to ACTH or fragments or variants thereof that are optionally complexed with other proteins (e.g., Bovine Serum Albumin), or metal ions, or charged polymers (e.g., polylysine), or fragments, homologs or analogs of ACTH, or any other suitable complexes that retain the functional characteristics of ACTH or ACTH fragments or analogs thereof and/or allow for formulation of ACTH or ACTH fragments or analogs thereof into suitable dosage forms.

In some embodiments, a synthetic adrenal corticotropin composition comprises an ACTH preparation. As used herein, "ACTH preparation" refers to a mixture containing ACTH peptide and/or other peptide fragments and/or other proteins and/or other substances that together form a composition that is suitable for any methods and/or dosing regimen described herein.

Synthetic adrenal corticotropin compositions are available commercially. For instance, Synacthen®, Adrenomone®, or the like. Further examples of commercially available synthetic adrenal corticotropin compositions may include and are not limited to Adrenocorticotropic Hormone (ACTH) (1-10) (human), Adrenocorticotropic Hormone (ACTH) (1-13) (human), Adrenocorticotropic Hormone (ACTH) (1-16) (human), Adrenocorticotropic Hormone (ACTH) (1-17) (human), Adrenocorticotropic Hormone (ACTH) (1-24) (human), Adrenocorticotropic Hormone (ACTH) (1-39) (human), Adrenocorticotropic Hormone (ACTH) (1-39) (rat), Adrenocorticotropic Hormone (ACTH) (18-39) (human), Adrenocorticotropic Hormone (ACTH) (4-10) (human), Adrenocorticotropic Hormone (ACTH) (1-4), Adrenocorticotropic Hormone (ACTH) (1-14) or the like available from, for example, GenScript.

(b) non-synthetic adrenal corticotropin composition

In certain embodiments of the present disclosure, an adrenal corticotropin treatment may comprise administration of a non-synthetic adrenal corticotropin composition. In these embodiments, ACTH is obtained from a cell that naturally, endogenously, produces an ACTH peptide, homolog, variant, aggregate, complex, preparation, or prodrug. For instance, a non-synthetic adrenal corticotropin composition may be prepared from a homogenized pituitary extract of an appropriate animal (e.g., pituitary extract of a pig). Any suitable method may be used to obtain a homogenized pituitary extract. In some embodiments, a homogenized pituitary extract includes ACTH peptide and/or other peptide fragments and/or other proteins and/or other substances that are contemplated as being part of the ACTH preparation that is compatible with any method described herein.

In one aspect, a non-synthetic adrenal corticotropin composition encompasses a repository corticotropin injection (RCI). An example of a repository corticotropin injection is Acthar® Gel (previously referred to as H.P. Acthar® Gel). Acthar® Gel is a naturally sourced complex mixture of adrenocorticotropic hormone analogs and other pituitary peptides. The Acthar® Gel manufacturing process converts the initial porcine pituitary extract with low ACTH content into a mixture having modified porcine ACTH and other related peptide analogs solubilized in gelatin. A major component in the formulated complex mixture is N-25 deamidated porcine ACTH (1-39). Acthar® Gel is supplied as a sterile preparation in 16% gelatin to provide a prolonged release after intramuscular or subcutaneous injection. Acthar® Gel also contains 0.5% phenol, not more than 0.1%

A cysteine (added), sodium hydroxide and/or acetic acid to adjust pH and water for injection.

In particular embodiments, a non-synthetic adrenal corticotropin composition of the present disclosure refers to a composition comprising N-25 deamidated porcine ACTH (1-39).

In certain embodiments, a repository corticotropin injection is administered intramuscularly. In some embodiments, the recommended regimen is a daily dose of 150 U/m2 (divided into twice daily intramuscular injections of 75 U/m2) administered over a 2-week period. Dosing can then be gradually tapered over a 2-week period to avoid adrenal insufficiency. The following is one suggested tapering schedule: 30 U/m2 in the morning for 3 days; 15 U/m2 in the morning for 3 days; 10 U/m2 in the morning for 3 days; and 10 U/m2 every other morning for 6-days.

In various embodiments, a respository corticotropin injection has a recommended dose for daily intramuscular or subcutaneous injections of 80-120 units for 2-3 weeks for acute exacerbations. In other embodiments, a repository corticotropin injection has a recommended dose of 40-80 units given intramuscularly or subcutaneously every 24-72 hours. Dosage should be individualized according to the medical condition of each patient. Frequency and dose of the drug should be determined by considering the severity of the disease and the initial response of the patient.

In embodiments where the repository corticotropin injection is Acthar® Gel, it should be noted that although drug dependence does not occur, sudden withdrawal of Acthar® Gel after prolonged use may lead to adrenal insufficiency or recurrent symptoms which make it difficult to stop the treatment. It may be necessary to taper the dose and increase the injection interval to gradually discontinue the medication.

In some embodiments, Acthar® Gel may be administered intramuscularly and a daily dose of 150 U/m2 (divided into twice daily intramuscular injections of 75 U/m$^2$) may be administered over a 2-week period. The dosing with Acthar® Gel can be gradually tapered over a 2-week period to avoid adrenal insufficiency. In one exemplary embodiment, a tapering schedule is as follows: 30 U/m$^2$ in the morning for 3 days; 15 U/m$^2$ in the morning for 3 days; 10 U/m$^2$ in the morning for 3 days; and 10 U/m$^2$ every other morning for 6-days.

Acthar® Gel is typically dosed based on body surface area (BSA). For calculation of body surface area, use the following formula:

$$BSA(m^2) = \sqrt{\frac{\text{weight (kg)} \times \text{height (cm)}}{3600}}$$

In other embodiments, Acthar® Gel may be administered intramuscularly or subcutaneous at doses of 80-120 units for 2-3 weeks for acute exacerbations. In still other embodiments, the dose of Acthar® Gel may be 40-80 units given intramuscularly or subcutaneously every 24-72 hours. In some embodiments, dosing is individualized according to the medical condition of each patient. Frequency and dose of the drug can be determined by considering the severity of the disease and the initial response of the patient.

Acthar® Gel is contraindicated for intravenous administration. Acthar® Gel is contraindicated where congenital infections are suspected in infants. Administration of live or live attenuated vaccines is contraindicated in patients receiving immunosuppressive doses of Acthar® Gel. Acthar® Gel is contraindicated in patients with scleroderma, osteoporosis, systemic fungal infections, ocular herpes simplex, recent surgery, history of or the presence of a peptic ulcer, congestive heart failure, uncontrolled hypertension, primary adrenocortical insufficiency, adrenocortical hyperfunction or sensitivity to proteins of porcine origin.

(c) Pharmaceutical compositions

The present disclosure also provides pharmaceutical compositions. A pharmaceutical composition comprises a synthetic adrenal corticotropin composition, a non-synthetic corticotropin composition, or a combination thereof. For instance, a pharmaceutical composition of the present disclosure may comprise a synthetic ACTH peptide, fragment, prodrug and variant, or any combination thereof, as an active ingredient, and at least one pharmaceutically acceptable excipient; alternatively, a pharmaceutical composition of the present disclosure may comprise a non-synthetic ACTH peptide, fragment, prodrug and variant, or any combination thereof, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, or a coloring agent. The amount and types of excipients utilized to form pharmaceutical compositions may be selected according to known principles of pharmaceutical science.

In each of the embodiments described herein, a composition of the invention may optionally comprise one or more additional drug or therapeutically active agent in addition to the adrenal corticotropin composition, prodrug and variant, or any combination thereof. Thus, in addition to the therapies described herein, one may also provide to the subject other therapies known to be efficacious for treatment of the disease, disorder, or condition.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylam ides, polyvinyloxoazolidone, polyvinylalcohols, C12-C18 fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The agents and compositions described herein can be formulated by any conventional manner using one or more pharmaceutically acceptable carriers or excipients as described in, for example, Remington's Pharmaceutical Sciences (A.R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in U.S. Pharmacopeia (USP 29) and National Formulary (NF 24), U.S. Pharmacopeial Convention, Inc., Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A.R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

(d) Administration (i) Dosage Forms

A composition of the present disclosure may be formulated into various dosage forms and administered by a number of different means that will deliver a therapeutically effective amount of the active ingredient.

In some embodiments, such compositions can be administered via inhalation, parenterally, topically, or in other suitable administration routes in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a cosmetic.

For embodiments where administration is by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carrier for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising an Adrenal corticotropin composition, prodrug, variant, or any combination thereof, is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the Adrenal corticotropin composition, prodrug, variant, or any combination thereof, in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, an Adrenal corticotropin composition, prodrug, variant, or any combination thereof may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9,12,15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride,1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the itaconate, malonate, derivatives thereof, an Adrenal corticotropin composition, and variant, or any combination thereof, may be prepared by any known method of preparing liposomes for drug delivery, such as, for example, detailed in U.S. Pat. Nos. 4,241,046; 4,394, 448; 4,529,561; 4,755,388; 4,828,837; 4,925,661; 4,954, 345; 4,957,735; 5,043,164; 5,064,655; 5,077,211; and 5,264, 618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of an Adrenal corticotropin composition, variant, or any combination thereof, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The compound of the itaconate, malonate, derivatives thereof, a compound of Formula (I), or a compound of Formula (II) may be encapsulated in a microemulsion by any method generally known in the art.

In yet another embodiment, an adrenal corticotropin composition, prodrug, variant, or any combination thereof, may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

Generally, a safe and effective amount of an adrenal corticotropin composition, prodrug, variant, or any combination thereof is, for example, that amount that would cause the desired therapeutic effect in a subject while minimizing undesired side effects.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the LD50 (the dose lethal to 50% of the population) and the ED50, (the dose therapeutically effective in 50% of the population). The dose ratio between toxic and therapeutic effects is the therapeutic index that can be expressed as the ratio LD50/ED50, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of an adrenal corticotropin composition can occur as a single event or over a time course of treatment. For example, an adrenal corticotropin composition can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities.

An adrenal corticotropin composition can be administered simultaneously or sequentially with another agent, such as an antibiotic, an anti-inflammatory, a pro-angiogenesis agent, or other agent. For example, an adrenal corticotropin composition can be administered simultaneously with another agent, such as a pro-angiogenesis agent. Simultaneous administration can occur through administration of separate compositions, each containing one or more of an adrenal corticotropin composition. Simultaneous administration can occur through administration of one composition containing two or more compositions. An adrenal corticotropin composition can be administered sequentially with an antibiotic, an anti-inflammatory, a pro-angiogenesis agent, or another agent. For example, an adrenal corticotropin composition can be administered before or after administration of a pro-angiogenesis agent, or another agent.

In some embodiments, one or more subsequent doses are administered every day, every other day, every two days, every three days, every four days, every 5 days, every 6 days, once a week, every two weeks, every three weeks, once a month, every six weeks, every two months, every three months, every four months, every five months, every six months or any combination thereof.

In some embodiments, a first dose of an adrenal corticotropin treatment is between about 10 IU, about 20 IU, about 30 IU, 40 IU, about 50 IU, about 60 IU, about 70 IU, 80 IU, about 90 IU, about 100 IU, about 110 IU, about 120 IU, about 130 IU, about 140 IU, about 150 IU about 200 IU, about 250 IU, about 300 IU, about 350 IU, about 400 IU, about 450 IU or about 500 IU, with reference to an ACTH peptide, fragment, or variant. In some embodiments, a first dose is between about 10 IU to about 400 IU, between about 10 IU to about 250 IU, between about 10 IU to about 100 IU, between about 10 IU to about 80 IU, between about 10 IU to about 60 IU, or between about 10 IU to about 40 IU. In some embodiments, a first dose is between about 10 IU to about 400 IU, between about 20 IU to about 400 IU, between about 40 IU to about 400 IU, between about 40 IU to about 350 IU, between about 40 IU to about 200 IU, between about 40 IU to about 100 IU, between about 40 IU to about 80 IU, or between about 40 IU to about 60 IU. In some embodiments, a first dose is between about 20 IU to about 200 IU, between about 60 IU to about 150 IU, between about 60 IU to about 100 IU, or between about 60 IU to about 80 IU.

In some embodiments, a one or more subsequent dose is between about 10 IU, about 20 IU, about 30 IU, 40 IU, about 50 IU, about 60 IU, about 70 IU, 80 IU, about 90 IU, about 100 IU, about 110 IU, about 120 IU, about 130 IU, about 140 IU, about 150 IU about 200 IU, about 250 IU, about 300 IU, about 350 IU, about 400 IU, about 450 IU or about 500 IU. In some embodiments, a one or more subsequent dose is between about 10 IU to about 400 IU, between about 10 IU to about 250 IU, between about 10 IU to about 100 IU, between about 10 IU to about 80 IU, between about 10 IU to about 60 IU, or between about 10 IU to about 40 IU. In some embodiments, a one or more subsequent dose is between about 10 IU to about 400 IU, between about 20 IU to about 400 IU, between about 40 IU to about 400 IU, between about 40 IU to about 350 IU, between about 40 IU to about 200 IU, between about 40 IU to about 100 IU, between about 40 IU to about 80 IU, or between about 40 IU to about 60 IU. In some embodiments, a one or more subsequent dose is between about 20 IU to about 200 IU, between about 60 IU to about 150 IU, between about 60 IU to about 100 IU, or between about 60 IU to about 80 IU.

In some embodiments, the pharmaceutical compositions described herein are in unit dosage forms suitable for single administration of precise dosages. In unit dosage form, the formulation is divided into unit doses containing appropriate quantities of an adrenal corticotropin treatment. In some embodiments, the unit dosage is in the form of a package containing discrete quantities of a formulation. Non-limiting examples are packaged tablets or capsules, powders in vials or ampoules, or injectable suspension or solution in ampoules. In some embodiments, aqueous suspension compositions are packaged in single-dose non-reclosable containers. Alternatively, multiple-dose reclosable containers are used. In some of such embodiments, a preservative is optionally included in the composition. By way of example only, formulations for intramuscular injection are presented in unit dosage form, which include, but are not limited to ampoules, or in multi dose containers, with an added preservative. In particular embodiments, Acthar® Gel may be administered via a self-injector device.

(e) combinations

Compositions disclosed herein may be administered in combination with one or more other therapeutic agents, such as chemotherapy drugs, radiation, monoclonal antibodies, immune cells such as T cells, immunosuppressive agents including cyclosporine, tacrolimus, CTLA-4Ig, TNF inhibitors, IL-1 receptor blockers, anti-CD20 antibodies, inhibitors of IL-6, inhibitors of IL-17, inhibitors of IL-23, immune checkpoint drugs, cyclophosphamide, methotrexate, azathioprine, glucocorticoids, anabolic steroids, anti-inflammatory agents including non-steroidal anti-inflammatory drugs, aspirin, colchicine, indomethacin, phenylbutazone, drugs that decrease plasma uric acid levels, volume repleting agents, anti-epileptics, drugs to treat diabetes, drugs to treat hypovolemic shock, drugs to treat multiple sclerosis, drugs to treat kidney disease, drugs to treat asthma, drugs to treat gout, drugs to treat arthritis, drugs to treat immunodeficiencies, drugs to treat GvHD, and drugs to treat osteoporosis. Such combination administration may be by means of a single dosage form which includes both a composition disclosed herein and one more other pharmaceutically active compounds, for example in a tablet, capsule, spray, inhalation powder, injectable liquid or the like. Alternatively, combination administration may be by means of administration of two different dosage forms, with one dosage form containing a composition disclosed herein, and the other dosage form including another pharmaceutically active compound. In this instance, the dosage forms may be the same or different. The term "co-administer" indicates that each of at least two compounds in the combination therapy are administered during a time frame wherein the respective periods of biological activity or effects overlap. Thus the term includes sequential as well as concurrent administration. In some embodiments, compositions disclosed herein can be chemically linked to other therapeutic agents prior to or for the purpose of co-administration. For example, compositions can be linked to, e.g., a monoclonal antibody or other protein, such as CTLA-4 Ig or etanercept. If more than one compound is co-administered, the routes of administration of the two or more compounds need not be the same.

II. METHODS

The present disclosure encompasses methods of modulating pericytes. Pericytes, as detailed above, are cells that wrap around endothelial cells of blood vessels. In particular, the present disclosure encompasses methods of increasing pericyte numbers or increasing pericyte longevity, or a combination thereof. As used herein, "increasing pericyte numbers" refers to increasing the absolute value of pericytes in a subject or cell culture system. Such an increase may arise from promoting cellular differentiation into the pericyte lineage, or by promoting an increase in pericyte cell division. Such numbers are measured in reference to pericyte numbers before contact with an adrenal corticotropin treatment of the present disclosure. As used herein, "increasing pericyte longevity" refers to protecting pericytes from damage, or inhibiting pericyte death, via apoptosis or other means, in a subject or cell culture system. In some embodiments, increasing pericyte longevity refers to decreasing pericyte apoptosis. In other embodiments, increasing pericyte longevity refers to protecting pericytes from damage, allowing for healthy vasculature beds. Methods of counting, measuring, or estimating pericyte numbers are known in the art.

Some embodiments of the present invention encompass methods of promoting new vessel formation in a subject, slowing vessel degradation in a subject, or increasing vessel stability in a subject. Methods of measuring, observing, or estimating new vessel formation, vessel degradation, or vessel stability are known in the art. For instance, while stable vessels exhibit normal endothelial cell fate markers, vascular instability is associated with endothelial-mesenchymal transition (EndMT) (see, for instance, Schwartz MA et al., A unifying concept in vascular health and disease. Science. 2018;360(6386):270-271, hereby incorporated by reference).

Certain embodiments of the present disclosure encompass methods of modulating growth factors and adhesion molecules that help maintain contact between pericytes and endothelial cells. For instance, the present disclosure may encompass methods of increasing angiopoietin-2 expression in pericytes, or increasing VCAM-1 expression in pericytes. Methods of measuring or estimating angiopoietin-2 expression or VCAM-1 expression in pericytes are known in the art.

The present invention also encompasses methods of stabilizing the blood brain barrier in a subject in need thereof.

In each of the embodiments discussed herein, the phrase "a subject in need thereof" refers to a subject in need of preventative or therapeutic treatment. A subject may be a human, a rodent, a livestock animal, a companion animal, or a zoological animal. In one embodiment, a subject may be a rodent, e.g., a mouse, a rat, a guinea pig, etc. In another embodiment, a subject may be a livestock animal. Non-limiting examples of suitable livestock animals may include pigs, cows, horses, goats, sheep, llamas and alpacas. In still another embodiment, a subject may be a companion animal. Non-limiting examples of companion animals may include pets such as dogs, cats, rabbits, and birds. In yet another embodiment, a subject may be a zoological animal. As used herein, a "zoological animal" refers to an animal that may be found in a zoo. Such animals may include non-human primates, large cats, wolves, and bears. In another preferred embodiment, a subject is a human.

In each of the embodiments detailed herein, a subject in need of treatment may be a subject diagnosed with one or more diseases, disorders, or conditions associated with vessel instability, injury, or deformation. Non-limiting examples of such diseases, disorders, or conditions may include diabetic retinopathy, central nervous system diseases, disorders or conditions characterized by loss of blood-brain barrier function, or macular degeneration For each of the methods detailed herein, the method encompasses contacting a pericyte with an adrenal corticotropin treatment as described in Section I above. A pericyte may be contacted with an adrenal corticotropin treatment in vitro, ex vivo, or in vivo. If in vivo, the subject is administered an adrenal corticotropin treatment as described in Section I above.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Chronic cuprizone model: Male C57BL/6 mice (6-8 wk) (Jackson laboratories, Bar Harbor, Me.) were fed with 0.2% cuprizone pellets (Envigo-Teklad Diet) for 12 weeks along with the control group with control pellets (Envigo-Teklad Diet). At the end of 12 weeks, they switched to control diet for another 3 weeks during which experimental groups were injected subcutaneously either with Acthar® Gel (3 U/kg, 10 U/kg, or 30 U/kg) or vehicle at 30 U/kg every other day. Control groups were injected with PBS only. Brains were collected at the end of 12 week of diet and then at the end of each week during injections.

Microvessel isolation—Microvessels were isolated from flash frozen brains of each group/treatment/time point following the technique established by Dr. Dore-Duffy (4). Briefly, tissues were homogenized with a glass tissue grinder, and following the myelin/fat tissue separation with 17% Dextran density gradient, the pellet of vessels passed through first a 100 um then a 70 um cell strainers to remove the larger vessels. The passed through microvessels were plated over coverslips and incubated in a culture medium overnight. Next day, the coverslips were washed with PBS and fixed with 4% PFA and then stained.

Oil Red: At various time points animals were euthanized and following tissue perfusion with PFA, brains were further incubated in 4% PFA overnight and then transferred to 20% sucrose for couple days before embedding into OCT and kept at −80° C. 40 um thick coronal brain sections were cut with a cryostat and stained with 0.5% Oil Red in propylene glycol for 8 min at 65° C. Sections were counterstained with hematoxylin before mounted with glycerol. Pictures were taken by a brightfield microscope (Leica DMLB).

Immunohistochemistry; Isolated microvessels first blocked with 5% normal donkey serum in PBS for 30 min. VCAM-1, VEGF, and Angiopoietin-2 (Ang2) immunostaining was visualized with using appropriate primary antibody and appropriate fluorochrome conjugated secondary antibody. Cells were visualized with nuclear satin DAPI, and pictures were taken by immunofluorescence microscope Leica DMLB.

To stain the vascular structures in the brain PFA fixed 10-um thick brain cryo-sections were first blocked with 5% normal donkey serum in PBS for 30 min. Glut-1+ immunostaining was visualized with using appropriate primary antibody and appropriate biotinylated secondary antibody. Using the Vectastain ABC and DAB substrate kit, staining procedure was completed. Glut+ vessels were counted under 10x magnification using Leica microscope.

Figures 1A, 1B:
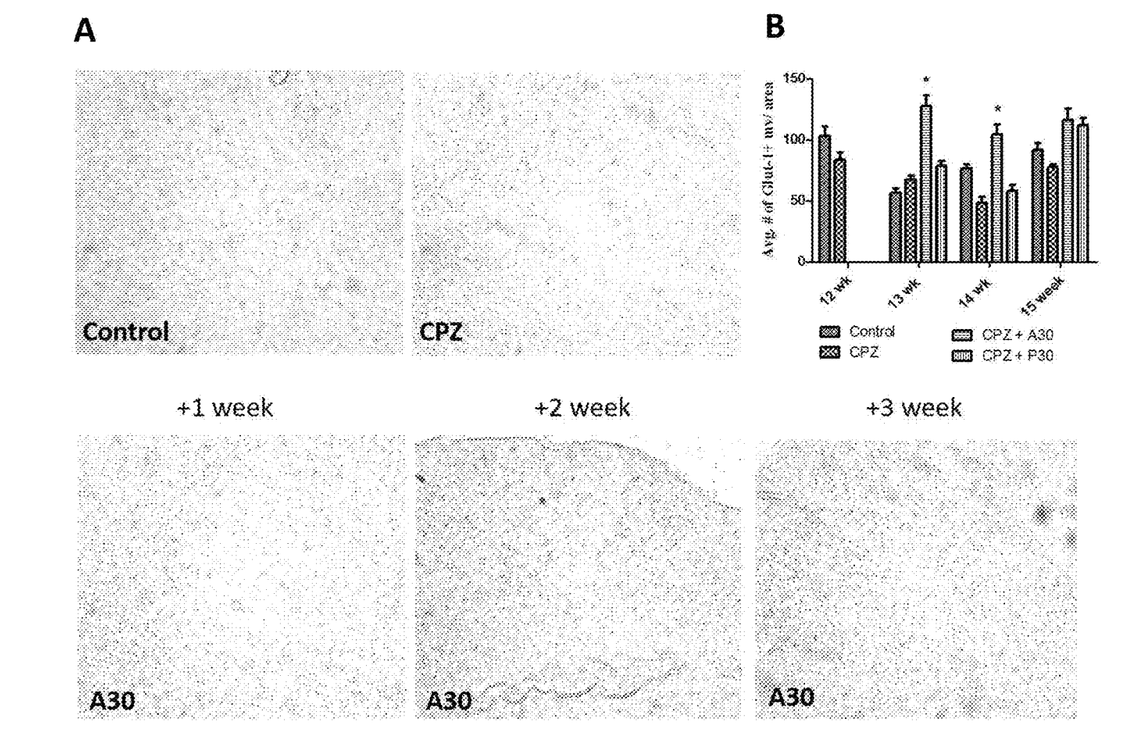
FIG. 1A and 1B: Acthar® Gel treatment induced Glut-1+ vessels. A) Brain sections were stained with Glut-1 antibody and visualized under light microscopy. Pictures represents 6-8 sections from each group/time point. B) The graph presents the mean ±SEM of Glut-1+ vessels counted blindly from 4 areas in each group/treatment/time point. The one-way ANOVA analysis revealed that the difference was statistically significant (p<0.001). Post-test Dunn's comparison among the groups revealed the significant difference between the Acthar® Gel treated and untreated groups; * p<0.05
Figure 2:
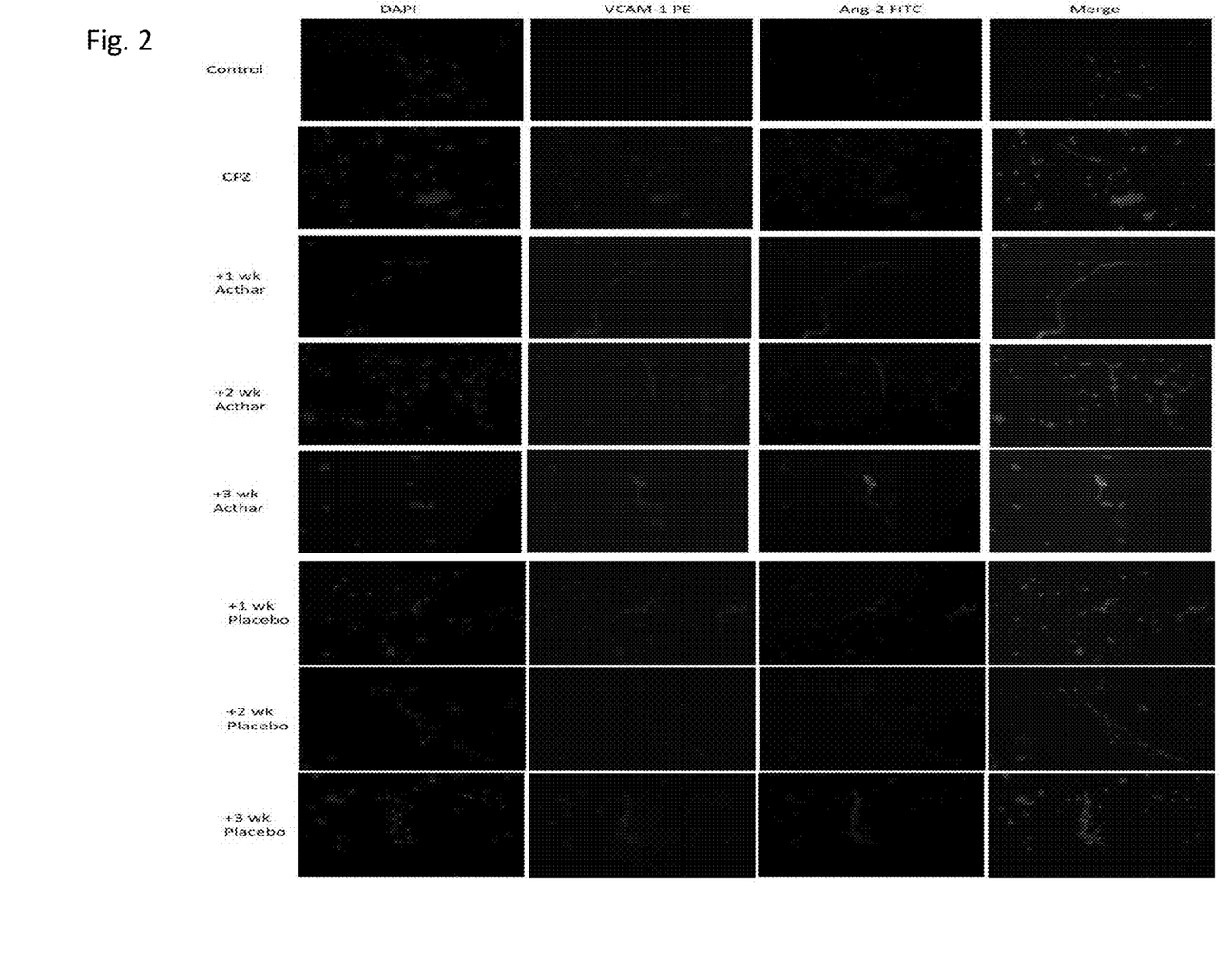
FIG. 2: Endothelial activation markers modulated with CPZ and Acthar® Gel treatment. The microvessels isolated from the brains of CPZ fed and drug treated mice were stained with vascular cell adhesion molecule (VCAM)-1 and Angiopoietin (Ang)-2 antibodies. VCAM-1 expression was induced after 12 week of CPZ diet compared to controls. Acthar® Gel 30 U/kg treatment continued to induce VCAM-1 during the 3 week treatment and also induced Ang-2 expression (consistent with the induction of new vessel formation) reaching to maximum after 3 weeks compared to both controls and Placebo Gel treated mice.

Results: In both the acute and chronic models of CIS vascular density is compromised. As in the acute model there was a significant decrease in vascular density during the 12 week ingestion protocol. The vessel number per mm square area, was significantly increased following treatment with Acthar® Gel. See FIGS. 1 and 2.

Example 2: Pericyte induction of neuron activity and pericyte differentiation (effect of Acthar® Gel).

Pericytes will be cultured with CAD cells at a one to one ratio. CAD cells alone, pericytes alone, CAD cells plus pericytes, CAD cells plus Acthar® Gel, pericytes plus Acthar® Gel and Co-cultures plus Acthar® Gel will be cultured in vitro with 3 concentrations of Acthar® Gel/ACTH for varying periods of time up to 3 weeks. Neuronal activity will be initially documented by immunohistochemistry and analysis of branching activity. Pericyte differentiation experiments will be performed in co-culture as well as in pericyte + growth factor experiments. Differentiation phenotype will be analyzed by immunocytochemistry and FACs analysis. Expression analysis will be performed on each group to determine potential changes in mRNA and proteomics.

Primary CNS pericytes will be examined for expression of MCsR by immunocytochemistry, FACs analysis and western analysis with and without agents known to augment expression of receptors. α-MSH is the endogenous agonists for the MC4R and is a linear peptide with 13 residues (Ac-Ser-Tyr-Ser-Met-Glu-His-Phe-Arg-Trp-Gly-Lys-Pro-Val-NH2). Substitution of Phe-7 and Met-4 for D-Phe and norleucine respectively yields NDP-α-MSH, which is a more potent MC4R agonist than α-MSH. NDP-α-MSH is available from Sigma (St Louis, Mo.). Preliminary evidence suggests that there may be subset difference in expression.

What is claimed is:

1. A method of promoting new vessel formation in a subject in need thereof, the method comprising administering an adrenal corticotropin treatment, wherein VCAM-1 expression and angiopoietin-2 expression is increased after the administering.

2. The method of claim 1, wherein the adrenal corticotropin treatment comprises a repository corticotropin injection (RCI).

3. The method of claim 2, wherein the repository corticotropin injection is a naturally sourced complex mixture of adrenocorticotropic hormone analogs and other pituitary peptides.

4. The method of claim 3, wherein the respository corticotropin injection comprises N-25 deamidated porcine ACTH (1-39).

5. The method of claim 1, wherein the adrenal corticotropin treatment is administered at a daily dose of 30-150 U/m2 over a 2-3 week period.

6. The method of claim 5, wherein the daily dose is gradually tapered over a 2 week period.

7. The method of claim 5, wherein peak VCAM-1 expression and angiopoietin-2 expression is after 3 weeks of administration.

8. A method of promoting new vessel formation in a subject in need thereof, the method comprising administering an adrenal corticotropin treatment to a subject in need thereof, wherein VCAM-1 expression and angiopoietin-2 expression is increased following 3 weeks of administering the adrenal corticotropin.

9. The method of claim 8, further comprising isolating a microvessel from the treated subject.

10. The method of claim 9, further comprising staining the isolated microvessel from the treated subject.

11. The method of claim 10, further comprising counting an increased number of vessels per square mm from the isolated microvessel.

12. The method of claim 8, wherein maximum angiopoietin-2 expression is reached after 3 weeks of administering the adrenal corticotropin.

* * * * *